United States Patent
Schmidt et al.

(10) Patent No.: US 7,141,700 B1
(45) Date of Patent: *Nov. 28, 2006

(54) DECOMPOSITION OF CUMENE HYDROPEROXIDE

(75) Inventors: Robert J. Schmidt, Barrington, IL (US); Russell C. Schulz, Glen Ellyn, IL (US); Patrick J. Bullen, Elmhurst, IL (US); Constante P. Tagamolila, Arlington Heights, IL (US); Steven P. Lankton, Wheeling, IL (US); Gary A. Peterson, Naperville, IL (US); Michael E. Fettis, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/207,842

(22) Filed: Aug. 19, 2005

(51) Int. Cl.
  *C07C 45/00* (2006.01)
  *C07C 37/08* (2006.01)
  *C07C 15/40* (2006.01)

(52) U.S. Cl. ............... 568/385; 568/411; 568/798; 585/435

(58) Field of Classification Search ............... None
See application file for complete search history.

(56) References Cited

U.S. PATENT DOCUMENTS

| | | | |
|---|---|---|---|
| 4,358,618 A | 11/1982 | Sifniades et al. | 568/385 |
| 6,201,157 B1 | 3/2001 | Keenan | 568/798 |
| 6,307,112 B1 | 10/2001 | Weber et al. | 568/798 |

OTHER PUBLICATIONS

Ljubicic, B., *Testing of Twisted-Tube Exchangers in Transition flow Regime* brochure from Brown Fintube Company, Koch Industries, 12602 FM 529, Houston, TX 77041, email: ljubicb@kochind.com.

*Primary Examiner*—Sikarl A. Witherspoon
(74) *Attorney, Agent, or Firm*—John G. Tolomei; James C. Paschall; John G. Cutts, Jr.

(57) ABSTRACT

A process for the decomposition of a cumene oxidation product mixture to produce phenol and acetone with reduced by-product formation by introducing the cumene oxidation mixture into an inlet of a decomposing vessel containing indirect heat exchange surfaces wherein the cumene oxidation product mixture and a circulating stream are admixed, reacted and cooled by passage around the indirect heat exchange surfaces.

18 Claims, 1 Drawing Sheet

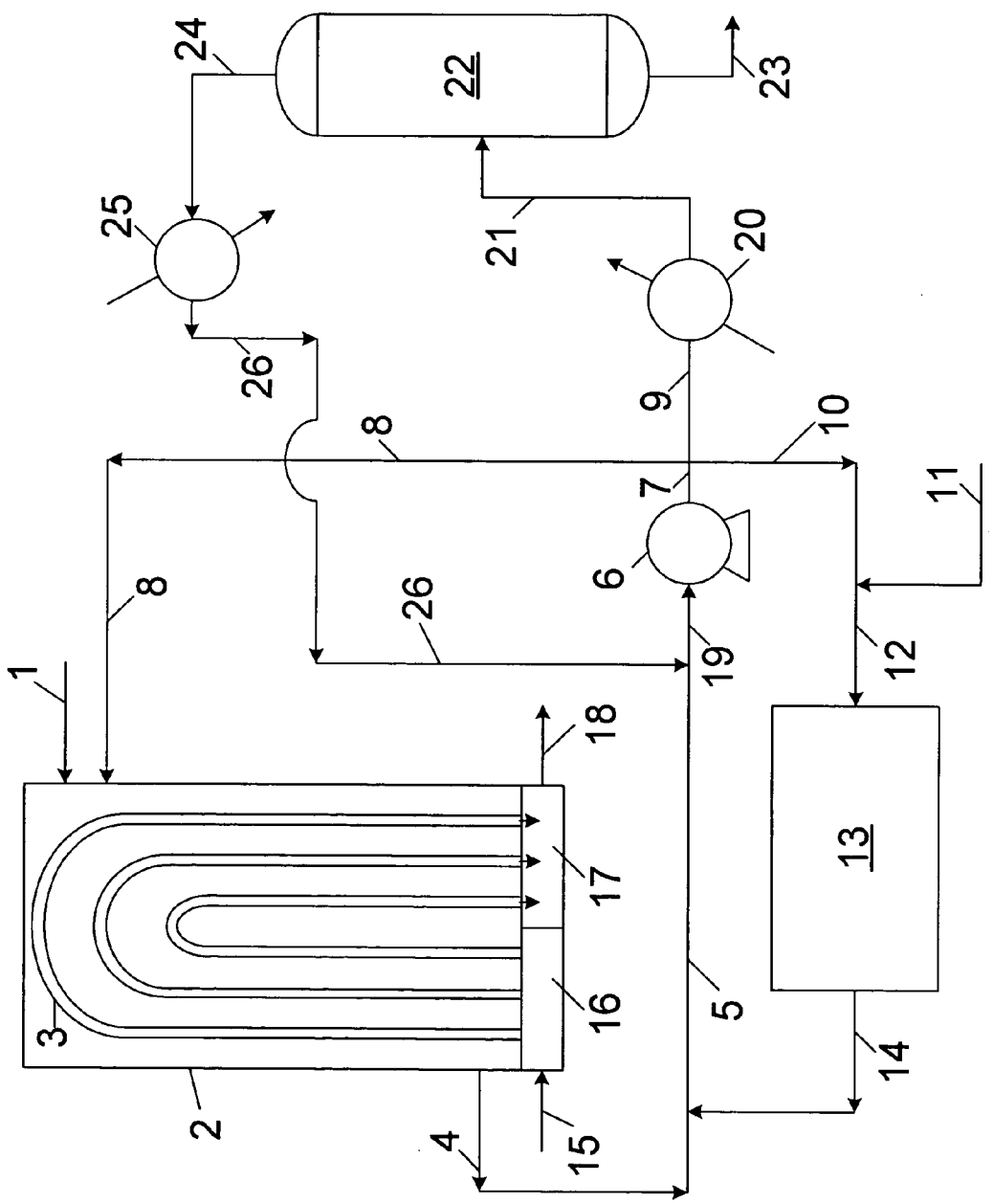

DECOMPOSITION OF CUMENE HYDROPEROXIDE

BACKGROUND OF THE INVENTION

Phenol is manufactured via air oxidation of cumene to cumene hydroperoxide (CHP), followed by acid-catalyzed cleavage of the latter to phenol and acetone, and known as CHP decomposition. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to alphamethylstyrene (AMS), a useful by-product. Very high yields of AMS can be obtained from pure DMPC, e.g., 98% yield upon dehydration over acidic silica at 300° C. In the presence of phenol, however, and more specifically in a phenol/acetone/cumene mixture which is a solvent in the decomposition of CHP/DMPC mixtures, the ultimate AMS yield is normally about 50–60 mol % of the DMPC. Main by-products are AMS dimers and cumylphenol which have no commercial value. Formation of cumylphenol also reduces the phenol yield.

Although phenol and acetone have been produced by the decomposition of the cumene oxidation product for decades, there is a continuing incentive to produce at a lower cost and with reduced by-product formation.

INFORMATION DISCLOSURE

U.S. Pat. No. 4,358,618 (Sifniades et al.) discloses a multi-step process for the production of acetone and phenol by the decomposition of cumene hydroperoxide.

U.S. Pat. No. 6,201,157 B1 (Keenan) discloses a process for the decomposition of cumene hydroperoxide using an acid catalyst and neutralizing the acid catalyst after the completion of the decomposition by the addition of an amine.

U.S. Pat. No. 6,307,112 (Weber et al.) discloses a process for cleaving cumene hydroperoxide wherein the mass flow ratio of a recycled partial product stream to the cumene hydroperoxide-containing feed stream sent to the cleavage reactor is less than 10. The patent discloses the use of vertical tube bundle heat exchangers.

A Brown Fintube Company Brochure discloses Twisted Tube® heat exchangers.

BRIEF SUMMARY OF THE INVENTION

The present invention is a process for the decomposition of a cumene oxidation product mixture comprising cumene hydroperoxide (CHP) to produce phenol and acetone with reduced by-product formation by introducing the cumene oxidation product mixture into an inlet of a decomposing vessel containing indirect heat exchange surfaces wherein the cumene oxidation product mixture and a circulating stream comprising cumene hydroperoxide, phenol, acetone and an acid catalyst are admixed, reacted and cooled by passage around the indirect heat exchange surfaces. The indirect heat exchange surfaces not only remove heat from the circulating stream which is exothermic, but serve to thoroughly admix the reactants which are undergoing decomposition to promote an isothermal flowing stream. A resulting reacted and cooled stream is continuously removed from the outlet of the decomposing vessel and at least a portion thereof is introduced into the inlet of the decomposing vessel. Another portion having a cumene hydroperoxide concentration from about 0.5 to about 5 weight percent is withdrawn for the subsequent recovery of phenol and acetone. In another embodiment, recovered acetone is recycled to the circulating stream.

BRIEF DESCRIPTION OF THE DRAWINGS

FIG. 1 is a schematic flow diagram of a preferred embodiment of the present invention for decomposing a cumene oxidation product mixture containing cumene hydroperoxide (CHP) and dimethylphenolcarbinol (DMPC) to produce phenol and acetone.

DETAILED DESCRIPTION OF THE INVENTION

It has been discovered that when a cumene oxidation product mixture containing cumene hydroperoxide (CHP) and DMPC is decomposed to produce phenol, acetone and alpha-methyl styrene by passing the cumene oxidation product mixture into a decomposing vessel containing indirect heat exchange surfaces wherein the cumene oxidation product mixture and an incoming circulating stream comprising cumene hydroperoxide, phenol, acetone and an acid catalyst are admixed, reacted and cooled by passage around the indirect heat exchange surfaces and then circulating a cooled stream comprising unreacted cumene hydroperoxide, phenol and acetone from the decomposing vessel to provide the circulating stream referred to hereinabove, an improved yield of alpha-methyl styrene is realized. A net reacted stream preferably comprising a cumene hydroperoxide concentration from about 0.5 to about 5 weight percent is removed from the circulating stream and recovered. The cumene oxidation product mixture is the result of cumene oxidation with oxygen and preferably comprises a cumene hydroperoxide concentration from about 60 to about 95 weight percent. The ratio of the flow rate of the cumene oxidation product mixture to the flow rate of the circulating stream is preferably from about 1:10 to about 1:100 in the decomposing vessel. In accordance with the present invention, a suitable and preferred acid catalyst is sulfuric acid.

The decomposing vessel is preferably operated at a temperature from about 50° C. (122° F.) to about 80° C. (176° F.) and a pressure from about 115 kPa (2 psig) to about 618 kPa (75 psig). The resulting effluent from the decomposing vessel is preferably introduced into a circulating stream preferably maintained at a temperature from about 50° C. (122° F.) to about 80° C. (176° F.) and a pressure sufficient to maintain a liquid phase. The decomposition of the cumene hydroperoxide is highly exothermic and therefore heat is removed from the decomposing vessel by indirect heat exchange surfaces to maintain the preferred operating temperature. Further, use of the indirect heat exchange surfaces disclosed herein allows the process to be maintained closer to an isothermal temperature condition which is beneficial and highly desirable to provide a high selectivity to desired products and to minimize undesirable byproducts.

The indirect heat exchange surfaces employed in the internal volume of the decomposing vessel may be any suitable type of known heat exchanger or exchangers. Suitable heat exchange surfaces include stab-in tube bundles, utilizing conventional baffle designs including segmental, helical and grid support systems, and twisted-tube heat exchangers. The indirect heat exchange surfaces may be oriented in any suitable orientation, i.e., vertical or horizontal, for example. The positioning of heat exchange surfaces within the decomposing vessel preferably maximizes the heat transfer efficiency and adequately admixes the entering stream of the cumene oxidation product mixture and the circulating stream comprising cumene hydroperoxide, an acid catalyst and phenol. The heat exchange surfaces not only provide heat removal but serve to admix the flowing contents of the decomposing vessel thereby minimizing any requirement for inline mixers, baffles, stirrers or the like. The internal location of the heat exchange surfaces enables the maintenance of an evenly and consistently controlled heat removal, low residence time and optimal placement which minimizes the overall area required for the plant.

A portion of the flowing liquid in the circulating stream, preferably containing from about 0.5 to about 5 weight percent cumene hydroperoxide, is removed from the circulating stream. Varying amounts of dicumyl peroxide (DCP) are also present in the removed portion and is preferably decomposed in a dehydrator to mainly yield phenol, acetone and alpha-methylstyrene (AMS) by increasing the temperature in the range from about 100° C. (212° F.) to about 170° C. (338° F.). The same higher temperature conditions that favor formation of AMS from DCP also favor the dehydration of dimethyl phenyl carbinol (DMPC) to AMS. It is therefore convenient to transform both the DMPC and the DCP present in the reaction mixture resulting from the acid catalyzed decomposition of CHP by simply heating that mixture to 100° C. (212° F.)–170° C. (338° F.) for a limited period of time in a plug-flow reactor referred to as a dehydrator. The dehydrator generally is composed of a heat exchanger in which the reaction mixture is brought up to the desired temperature, in series with a pipe or baffled tank, in which the reaction is completed. The latter part of the reactor is essentially isothermal. The yield of AMS formed in the reaction increases with time as DCP and the residual DMPC decompose, until it reaches a maximum and then decreases as AMS reacts further to form AMS dimers and cumylphenol. The optimum reaction time depends on the temperature and the concentrations of acid catalyst and water present in the mixture. Generally, shorter times are required at higher temperatures and in the presence of higher concentrations of acid and lower concentrations of water.

In accordance with one embodiment, after the decomposition reaction of the CHP is completed in the dehydrator, the resulting effluent therefrom is introduced into a flash drum to vaporize at least a portion of the acetone which is subsequently condensed and introduced into the circulating stream. The flash drum is preferably operated at a temperature from about 50° C. (122° F.) to about 150° C. (302° F.) and pressure from about 115 kPa (2 psig) to about 618 kPa (75 psig). The acetone is preferably recycled, serving as a diluent, and introduced into the circulating stream wherein the weight ratio of the acetone recycle to the cumene oxidation product mixture is in the range from about 0.1:1 to about 2:1. A resulting liquid stream comprising phenol and acetone is removed from the flash drum and fractionated to further separate the products including phenol and acetone.

DETAILED DESCRIPTION OF THE DRAWINGS

A cumene oxidation product mixture is introduced into the process via line 1 into decomposing vessel 2. A circulating stream comprising cumene hydroperoxide, an acid catalyst, phenol and acetone is introduced into decomposing vessel 2 via line 8. The two hereinabove described streams which are introduced into decomposing vessel 2 pass through decomposing vessel 2 while contacting indirect heat exchange surfaces 3. A resulting admixed and cooled inventory in decomposing vessel 2 is removed therefrom via line 4. A coolant is introduced into chamber 16 via line 15 and flows into indirect heat exchange surfaces 3. A resulting coolant which has been heated by the flowing contents of decomposing vessel 2 is passed from indirect heat exchange surfaces 3 into chamber 17. A resulting heated coolant is removed from chamber 17 via line 18 and recovered. The heated coolant may be cooled and recycled to indirect heat exchange surfaces 3. The reacted flowing stream which was removed from decomposing vessel 2 via line 4 is carried via lines 5 and 19 and introduced into pump 6. The resulting pressurized stream is carried from pump 6 via line 7 and a portion is further carried via line 8 and introduced into decomposing vessel 2 as described hereinabove. Another portion of the pressurized circulating stream from pump 6 and carried via line 7 is carried via line 10 and is admixed with an acid catalyst which is introduced via line 11. The resulting mixture containing the acid catalyst is carried via line 12 and introduced into calorimeter 13 which is used to monitor and control the operating conditions for the decomposition of the CHP. A resulting stream is removed from calorimeter 13 via lines 14, 5 and 19 and is passed into pump 6 as hereinabove described. Another portion of the pressurized stream from pump 6 is carried via lines 7 and 9 and introduced into heat exchanger 20 to be heated. A resulting heated stream is removed from heat exchanger 20 via line 21 and introduced into flash drum 22. A vapor stream comprising acetone is removed from flash drum 22 via line 24 and introduced into heat exchanger 25 for cooling. A resulting cooled and condensed stream comprising acetone is removed from heat exchanger 25 via line 26 and is introduced into pump 6 via lines 26 and 19. A resulting stream comprising acetone and phenol is removed from flash drum 22 via line 23 and recovered.

ILLUSTRATIVE EMBODIMENT

A cumene oxidation product mixture containing an 88.5 weight percent cumene hydroperoxide (CHP) in an amount of 26 m³/hr is introduced into a decomposer vessel containing heat exchange surfaces sufficient to maintain a desired temperature during the exothermic decomposition of CHP to produce phenol and acetone. The contents of the decomposer include CHP, an acid catalyst, phenol and acetone and are circulated in an external flowing loop and re-introduced into the decomposer. The external flowing loop is circulated at a flow rate of about 26 m³/hr and contains a sulfuric acid level of about 6 wppm and maintained at a temperature of about 75° C. (167° F.). The residence time of the cumene oxidation product mixture in the decomposer and the external flowing loop is about 15 minutes. A decomposer product stream containing a CHP concentration of about 3 weight percent is removed from the external flowing loop and is passed through a dehydrator operated at a temperature of 135° C. (275° F.). The resulting AMS yield is 85.5 mol % and the feed cumene/phenol yield weight ratio is 1.290. Thus, the weight yield ratio is now very close to the theoretical limit for this type of chemistry of 1.277. The feed cumene/phenol yield mol ratio is 0.989.

The foregoing description, drawing and illustrative embodiment clearly illustrate the advantages encompassed by the process of the present invention and the benefits to be afforded with the use thereof.

What is claimed is:

1. A process for decomposing a cumene oxidation product mixture containing cumene hydroperoxide (CHP) and dimethylphenylcarbinol (DMPC) to produce phenol, acetone, and alpha-methyl styrene (AMS) with reduced by-product formation which comprises:
   (a) introducing the cumene oxidation product mixture into a decomposing vessel containing indirect heat exchange surfaces wherein the cumene oxidation product mixture and a hereinafter described incoming circulating stream comprising cumene hydroperoxide, phenol, acetone and an acid catalyst are admixed, reacted and cooled by passage around the indirect heat exchange surfaces;
   (b) circulating a cooled stream comprising unreacted cumene hydroperoxide, phenol and acetone from the decomposing vessel to provide the circulating stream of step (a); and
   (c) withdrawing a reacted stream comprising a cumene hydroperoxide concentration from about 0.5 to about 5 weight percent from the circulating stream.

2. The process of claim 1 wherein the indirect heat exchange surfaces are selected from the group consisting of tubes, plates and grids.

3. The process of claim 1 wherein the decomposing vessel is operated at a temperature from about 50° C. (122° F.) to about 80° C. (176° F.) and a pressure from about 115 kPa (2 psig) to about 618 kPa (75 psig).

4. The process of claim 1 wherein the cumene oxidation product mixture comprises a cumene hydroperoxide concentration from about 60 to about 95 weight percent.

5. The process of claim 1 wherein the ratio of the flow rate of the cumene oxidation product mixture to the flow rate of the circulating stream is from about 1:10 to about 1:100.

6. The process of claim 1 wherein the acid catalyst is sulfuric acid.

7. A process for decomposing a cumene oxidation product mixture containing cumene hydroperoxide (CHP) and dimethylcarbinol (DMPC) to produce phenol, acetone and alpha-methyl styrene (AMS) with reduced by-product formation which comprises:
   (a) introducing the cumene oxidation produce mixture into a decomposing vessel containing indirect heat exchange surfaces wherein the cumene oxidation product mixture and a hereinafter described incoming circulating stream comprising cumene hydroperoxide, phenol, acetone and an acid catalyst are admixed, reacted and cooled by passage around the indirect heat exchange surfaces;
   (b) circulating a cooled stream comprising unreacted cumene hydroperoxide, phenol and acetone from the decomposing vessel to provide the circulating stream of step (a);
   (c) withdrawing a reacted stream comprising acetone and cumene hydroperoxide having a concentration from about 0.5 to about 5 weight percent from the circulating stream;
   (d) recovering at least a portion of the acetone from the reacted stream; and
   (e) recycling at least a portion of the acetone recovered in step (d) to the circulating stream in step (a).

8. The process of claim 7 wherein the indirect heat exchange surfaces are selected from the group consisting of tubes, plates and grids.

9. The process of claim 7 wherein the decomposing vessel is operated at a temperature from about 50° C. (122° F.) to about 80° C. (176° F.) and a pressure from about 115 kPa (2 psig) to about 618 kPa (75 psig).

10. The process of claim 7 wherein the cumene oxidation product mixture comprises a cumene hydroperoxide concentration from about 60 to about 95 weight percent.

11. The process of claim 7 wherein the ratio of the flow rate of the cumene oxidation product mixture to the flow rate of the circulating stream is from about 1:10 to about 1:100.

12. The process of claim 7 wherein the acid catalyst is sulfuric acid.

13. The process of claim 7 wherein the weight ratio of the acetone recycle to the cumene oxidation product mixture is in the range from about 0.1:1 to about 2:1.

14. The process of claim 7 wherein the recovery of acetone in step (d) is conducted in a flash drum.

15. A process for decomposing a cumene oxidation product mixture containing cumene hydroperoxide (CHP) and dimethylcarbinol (DMPC) to produce phenol, acetone and alpha-methyl styrene (AMS) with reduced by-product formation which comprises:
   (a) introducing the cumene oxidation product mixture having a cumene hydroperoxide concentration from about 60 to about 95 weight percent into a decomposing vessel containing indirect heat exchange surfaces wherein the cumene oxidation product mixture and a hereinafter described incoming circulating stream comprising cumene hydroperoxide, phenol, acetone and a sulfuric acid catalyst are admixed, reacted and cooled by passage around the indirect heat exchange surfaces wherein the decomposing vessel is operated at a temperature from about 50° C. (122° F.) to about 80° C. (176° F.) and a pressure from about 115 kPa (2 psig) to about 618 kPa (75 psig);
   (b) circulating a cooled stream comprising unreacted cumene hydroperoxide, phenol and acetone from the decomposing vessel to provide the circulating stream of step (a);
   (c) withdrawing a reacted stream comprising acetone and cumene hydroperoxide having a concentration from about 0.5 to about 5 weight percent from the circulating stream;
   (d) recovering at least a portion of the acetone from the reacted stream; and
   (e) recycling at least a portion of the acetone recovered in step (d) to the circulating stream in step (a).

16. The process of claim 15 wherein the indirect heat exchange surfaces are selected from the group consisting of tubes, plates and grids.

17. The process of claim 15 wherein the ratio of the flow rate of the cumene oxidation product mixture to the flow rate of the circulating stream is from about 1:10 to about 1:100.

18. The process of claim 15 wherein the weight ratio of the acetone recycle to the cumene oxidation product mixture is in the range from about 0.1:1 to about 2:1.

* * * * *